(12) United States Patent
Kusibojoska et al.

(10) Patent No.: US 6,648,871 B2
(45) Date of Patent: Nov. 18, 2003

(54) ABSORBENT ARTICLE AND A METHOD FOR ITS MANUFACTURE

(75) Inventors: Liljana Kusibojoska, Halsingborg (SE); Kent Hermansson, Västra Frölunda (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/954,163

(22) Filed: Sep. 18, 2001

(65) Prior Publication Data

US 2002/0045881 A1 Apr. 18, 2002

Related U.S. Application Data

(60) Provisional application No. 60/233,420, filed on Sep. 18, 2000.

(30) Foreign Application Priority Data

Sep. 18, 2000 (SE) .............................................. 0003331

(51) Int. Cl.[7] .............................................. A61F 13/15
(52) U.S. Cl. .................................. 604/392; 604/385.04
(58) Field of Search ................................. 604/386, 387, 604/389, 390, 392, 385.03, 385.04

(56) References Cited

U.S. PATENT DOCUMENTS

| | | | |
|---|---|---|---|
| 1,614,239 A | | 1/1927 | Hammond |
| H1440 H | * | 5/1995 | New et al. .................. 604/386 |
| 5,423,789 A | * | 6/1995 | Kuen ......................... 604/386 |
| 5,706,524 A | * | 1/1998 | Herrin et al. ................. 2/400 |
| 5,906,604 A | * | 5/1999 | Ronnberg et al. ........... 604/386 |
| 5,971,970 A | * | 10/1999 | Carlbark et al. ....... 604/385.03 |
| 6,051,094 A | | 4/2000 | Melbye et al. |
| 6,413,249 B1 | * | 7/2002 | Turi et al. .................. 604/387 |
| 6,494,873 B2 | * | 12/2002 | Karlsson et al. ............ 604/392 |

FOREIGN PATENT DOCUMENTS

| | | |
|---|---|---|
| EP | 0 287 388 A2 | 10/1988 |
| EP | 0 409 307 B1 | 1/1991 |
| EP | 0 605 012 B1 | 7/1994 |
| FR | 2 586 558 | 3/1987 |
| JP | A 9-253123 | 9/1997 |
| JP | A 10-314228 | 12/1998 |
| WO | 86/04812 | 8/1986 |
| WO | 91/08725 | 6/1991 |
| WO | 95/29657 | 11/1995 |

* cited by examiner

*Primary Examiner*—Weilun Lo
*Assistant Examiner*—Michael G Bogart
(74) *Attorney, Agent, or Firm*—Young & Thompson

(57) ABSTRACT

Absorbent article provided with a pair of belt members intended to be fastened together around the waist of the wearer and where the front portion is provided with fastening elements intended to be fastened to the belt members, such that the article will assume a pantlike shape, where the belt members form a part of the waist portions of the pant. The belt members are before use double-folded and cut in an arcuate shape whose tangent to the arcuate curve formed by respective longitudinal edges of the belt members in the area of the fold makes a substantially right angle to the fold. The folded belt members are applied to the rear portion of the article, and when the article is to be used they are unfolded, and form an arcuate shape where the portions on either sides of the fold are the mirror image of each other.

6 Claims, 3 Drawing Sheets

ABSORBENT ARTICLE AND A METHOD FOR ITS MANUFACTURE

TECHNICAL FIELD

The present invention refers to an absorbent article such as a diaper and an incontinence guard comprising a liquid permeable topsheet, a liquid impermeable backsheet and an absorbent body enclosed therebetween, said article having a front portion, a rear portion and a crotch portion therebetween, and further is provided with a pair of belt members attached to the rear portion, alternatively the front portion, of the article and which are intended to be fastened together around the waist of the wearer and where said front portion, alternatively said rear portion, is provided with fastening means intended to be fastened to the belt members, in such a way that the article will assume a pantlike shape, where the belt members form a part of the waist portions of the pant. The invention also refers to a method for manufacturing the article.

BACKGROUND OF THE INVENTION

Diapers and incontinence guards for incontinent adults usually have a garment portion holding an absorbent body in place against the user's body and attachment means which hold the garment portion in place also when the user is moving. A common type of attachment means are adhesive tapes or hook and loop fasteners of the touch-and-close type which directly attach the front and rear portions of the absorbent article to each other. It is further known, through e g EP-A-0 287 388, EP-A-0 409 307, EP-A-0 605 012 and FR-A-2 586 558, to attach the front and rear portions of the article by means of a belt, at which the possibilities to adjust the fit are improved. The belt further provides a simplified change of diaper or incontinence guard, especially when the wearer is standing.

The ends of the belt members can however be difficult to grasp when the article shall be applied to a wearer, especially if the wearer is lying down and the belt ends get caught under the wearer. Besides the long belt ends may cause processability problems during the manufacturing of the article. It is therefore a desire that the belt ends before use are folded and gathered at an easily accessible location on the article.

The belt members are usually straight. It has however proven that a belt having an arcuate shape sometimes can give an improved fit around the waist of the wearer. Such an arcuate belt is known through WO 91/08725. This document does however not give any solution to the problem of prefolding the belt members during manufacture.

Through WO 86/04812 it is previously known to fold the attachment straps of a diaper, i e the straps that carry the attachment means that fasten up the front and rear portions of the diaper, in accordion-like fashion before they are applied to the diaper in order to simplify manufacture and packaging of the products. The folded attachment straps are kept together by a weak adhesive applied in narrow zones in order to be easily released and unfolded when the diaper is ready for use. The attachment straps are straight and do not constitute a belt as defined in the present invention.

OBJECT AND MOST IMPORTANT FEATURES OF THE INVENTION

The object of the present invention is to accomplish a belt-provided absorbent article, such as a diaper or incontinence guard, said belt having an arcuate shape with improved fit accomplished by simple manufacturing steps, said belt members being folded for improving their handling during the manufacturing process and the application of the product on the user. This has according to the invention been solved by the fact that the belt members before use are double-folded and cut in an arcuate shape in which the tangent to the arcuate curve formed by the respective longitudinal edges of the belt members, in the area of the fold makes a substantially right angle to the fold, that the belt members in their double folded condition are applied to the rear portion of the article, and that they when the article is to be used are intended to be unfolded, at which the belt members in their unfolded position form an arcuate shape where the portions on either sides of the fold are the mirror image of each other.

According to a preferred embodiment the belt members are held in place in their double-folded position against the rear portion of the article by means of an easily breakable seal.

The invention also refers to a method for manufacturing a belt-provided article, at which the belt portions before they are applied to the article are folded double and then cut in an arcuate shape, where the tangent to the arcuate curve formed by the respective longitudinal side edges of the belt members, in the area of the fold make a substantially right angle to the fold, and that the belt members in their double folded position are applied to the rear portion of the article.

Företrädesvis fästs bältesdelarna till alstrets bakre parti i sitt dubbelvikta tillstämedelst en lätt brytbar försegling.

DESCRIPTION OF DRAWINGS

The invention will in the following be closer described with reference to an embodiment shown in the accompanying drawings.

DESCRIPTION OF AN EMBODIMENT

Figure 1:
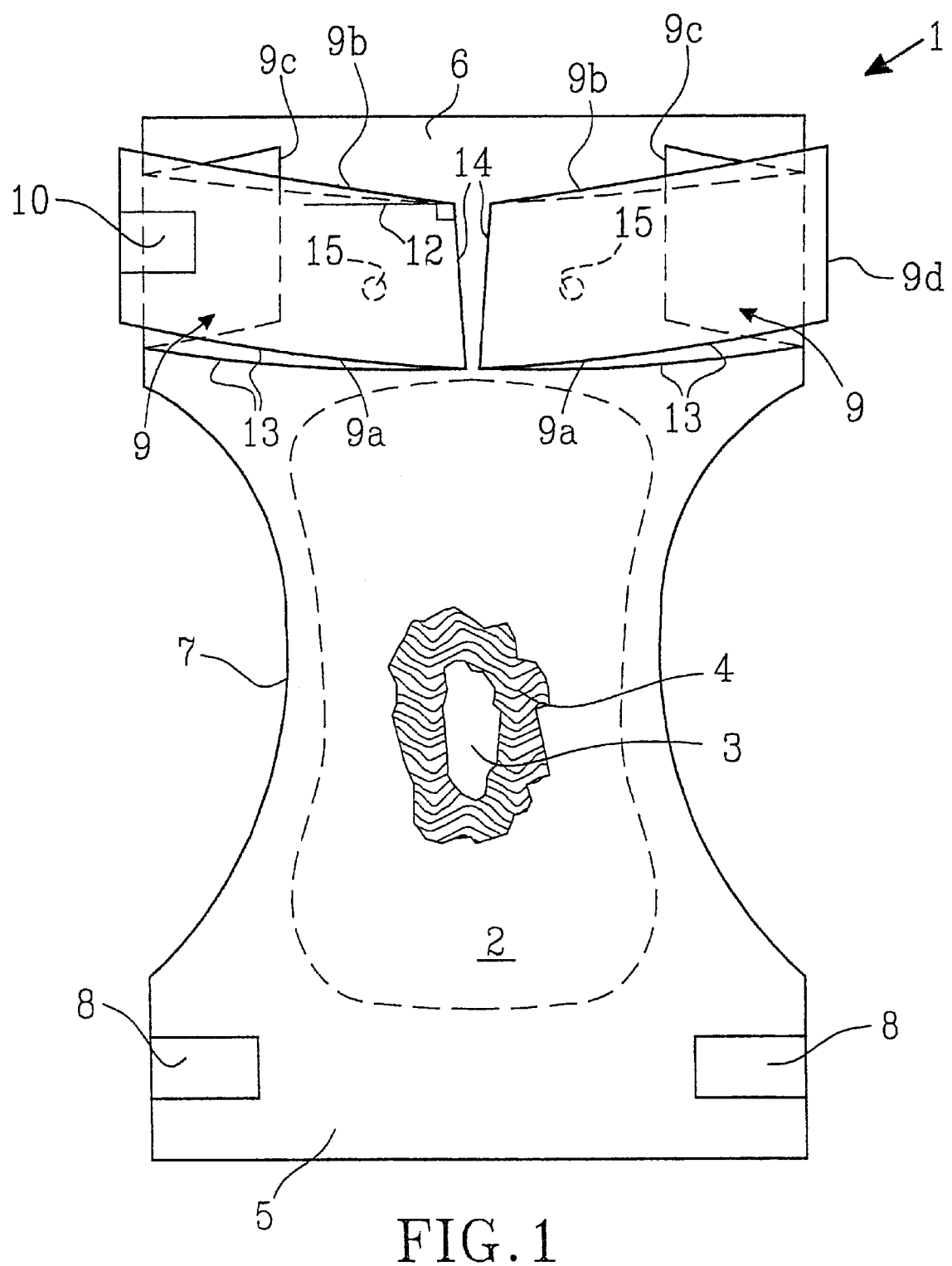
FIG. 1 shows schematically a perspective view of a diaper or incontinence guard according to the invention having the belt portions folded.
Figure 2:
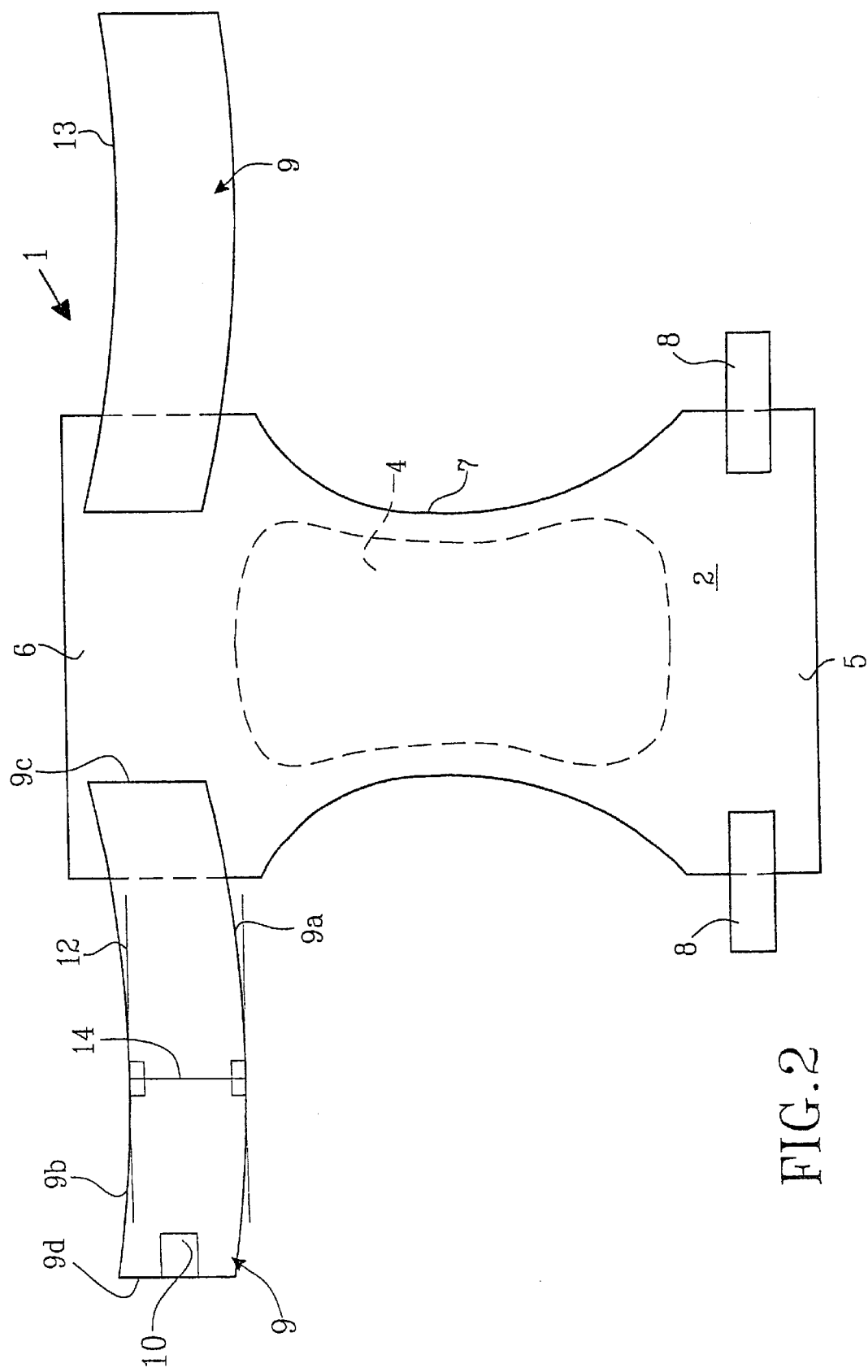
FIG. 2 shows the diaper according to FIG. 1 but having the belt portions extended and unfolded.

FIGS. 1 and 2 shows an embodiment of a diaper or incontinence guard 1 comprising a liquid permeable topsheet 2, a liquid impermeable backsheet 3 and an absorbent body 4 enclosed therebetween. The liquid permeable topsheet 2 can consist of a nonwoven material, e g a spunbond material of continuous filaments, a meltblown material or a bonded carded fibrous web. The liquid impermeable backsheet 3 may consist of a plastic film, a nonwoven material coated with a liquid impervious material or a hydrophobic nonwoven material which resists liquid penetration.

The topsheet 2 and the backsheet material 3 has a somewhat greater extension in the plane than the absorbent body 4 and extends outside the edges thereof. The layers 2 and 3 are connected to each other within the projecting portions thereof, e g by gluing or welding by heat or ultrasonic.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well-known to the person skilled in the art and does therefore not have to be described in detail. The thin absorbent bodies which are common in for example baby diapers and incontinence guards often comprise a compressed mixed or layered structure of cellulosic fluff pulp and superabsorbent.

The diaper/incontinence guard is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of adhesive tape portions 8 or other type of attachment means such as hooks and loops fasteners of the touch-and-close type.

A pair of belt members 9 are with one end attached, e g glued or ultrasonically welded, to the rear portion 5 of the diaper. The belt members 9 are with their opposite ends intended to be fastened together, e g by means of tape tab 10 which is taped against the outside of the opposite belt member. Instead of a tape tab there may be another optional attachment means, such as hook-and-loop type fasteners. The attachment tapes 8 of the front portion 5 or corresponding attachment means are intended to be attached against the outsides of the belt members 9 in order to fasten together the diaper/incontinence guard to the desired pantlike shape. The belt members have opposed longitudinal side edges 9a,b and end edges 9c,d, at which one end edge 9c is attached to the rear portion of the diaper and the other end edge 9d of one belt portion carries said fastening means 10.

The width of the belt members 9 should be between 5–20 cm, preferably between 7–15 cm.

The belt members 9 are preferably a laminate of a carrier material, which forms the outside of the belt, and a soft nonwoven, which forms the inside of the belt intended to be in direct contact with the skin of the user.

A suitable nonwoven material can be a spunbond material of e g polypropylene- or polyethylene fibres. Conjugate fibres may also be used. Another suitable nonwoven material can be a carded thermobonded material of e g polypropylene-, polyester- or conjugate fibres.

As a carrier material there can be used a plastic film or another appropriate material, e g a nonwoven. The carrier material should be adapted to function as a reception surface for the attachment means 8 and 10, at which in those cases the attachment means are tape tabs, a plastic film is suitable. In case other types of attachment means are used instead of tape tabs, e g hook-and-loop type fasteners, another type of carrier material is suitable which may function as a reception surface for the attachment means in question. Also elastic laminates are suitable to use as material in the belt portions.

Figure 3:
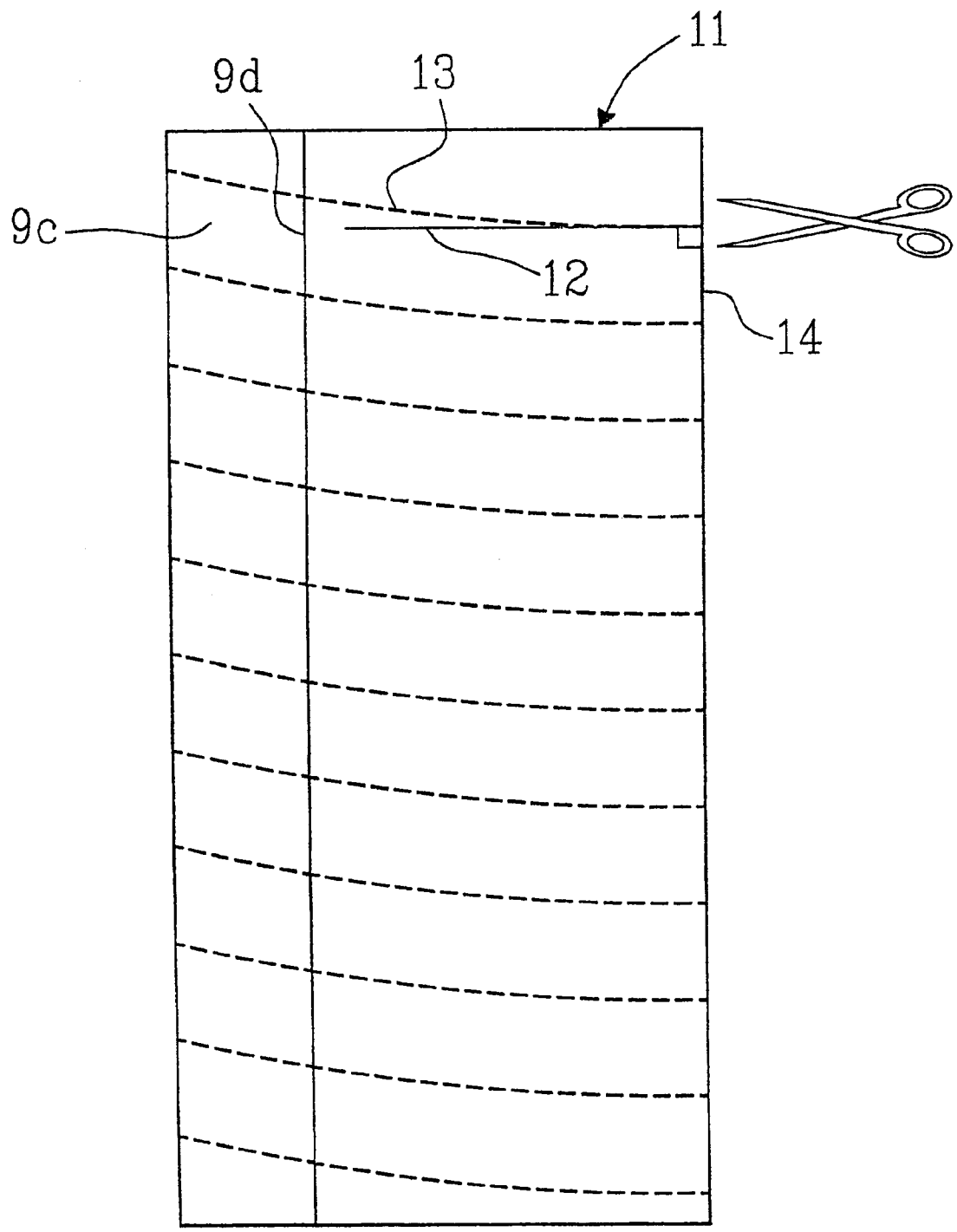
FIG. 3 shows schematically the manufacture of the belt members by cutting a double-folded piece of material.

The belt members 9 are before use double folded and cut in the shape of half an arch. This is made, as is shown in FIG. 3, by folding a piece of material, which is intended to form the belt members 9, together and then cutting the double folded material in the shape of half an arch, in such a way that the tangent 12 to the arcuate curve 13 formed by the respective cutting line in the area of the fold 14 make a substantially right angle to the fold. Said cutting lines will form the longitudinal side edges 9a and b of the belt members. By this the belt members will in their unfolded extended position form an arch-shape where the portions on opposite sides of the fold 14 are the mirror image of each other. A plurality of belt members can be cut from the same piece of material 11 without waste of material therebetween. Preferably the fold 14 is placed so that the belt member on one side of the fold 14 will be longer than on the other side of the fold. The longer projecting end can by this make the end 9c which is attached to the rear portion 6 of the diaper. It is also possible, in case a long belt is desired, to place the fold 14 so that the belt members are equally long on both sides of the fold or even so that the longer projecting end makes the end 9d which is to be attached to the opposite belt member. By this said end 9d will project outside the side edges of the rear portion 6 or alternatively be folded back over this.

The belt members 9 are in their folded position with one end edge 9c and the portions adjacent thereto attached to the rear portion 6 of the diaper in a known manner. The belt members 9 are then folded in towards the rear portion 6 and preferably attached in this position by an easily breakable seal 15, such as a glue string/glue dot or welding seam/welding dot provided by ultrasonic or heat.

When the diaper/incontinence guard is to be applied on the wearer the belt members 9 are easily accessible to the nurse and by a light jerk in the belt end 9d the seal 15 is broken and the belt members 9 can be unfolded and fastened together around the waist of the wearer. The belt members 9 have as shown in FIG. 2 an arcuate shape, which gives an improved fit around the waist of the wearer. The fastening means 8 on the front portion 5 can then be attached to the outside of the belt members 9 in order to fasten together the diaper/incontinence guard to the desired pantlike shape.

The invention is of course not limited to the above described embodiment but can be modified within the scope of the claims.

What is claimed is:

1. An absorbent article comprising:

a liquid permeable top sheet, a liquid impermeable back sheet and an absorbent body enclosed therebetween;

said article having a front portion, a rear portion and a crotch portion therebetween;

a pair of belt members attached to one of the rear portion and the front portion of the article; said belt members intended to be fastened together around the waist of the wearer;

one of said front portion and said rear portion being provided with fastening means intended to be fastened to the belt members, such that the article will assume a pant shape, where the belt members form a part of the waist portions of the pant;

wherein before use, the belt members are double-folded and cut in an arcuate shape in which a tangent to the arcuate curve formed by respective longitudinal edges of the belt members in the area of the fold makes a substantially right angle to the fold; the belt members in their double folded position are applied to the rear portion of the article; and when the article is to be used, said belt members are intended to be unfolded into two portions on either sides of the fold, at which the belt members in their unfolded position form an arcuate shape where the portions on either sides of the fold are mirror images of each other.

2. The absorbent article according to claim 1, wherein the belt members are kept in place in their double folded position against the rear portion of the article by an easily breakable seal.

3. The absorbent article according to claim 1, wherein each of the longitudinal edges of the belt members present in the double folded position, a single smooth arcuate curve.

4. The absorbent article according to claim 1, wherein each of the longitudinal edges of the belt members present in the unfolded position, a single smooth arcuate curve.

5. A method for manufacturing an absorbent article comprising a liquid permeable top sheet, a liquid impermeable back sheet and an absorbent body enclosed therebetween; said article having a front portion, a rear portion and a crotch portion therebetween; a pair of belt members attached to the rear portion of the article; said belt members intended to be fastened together around the waist of a wearer; said front portion being provided with fastening means intended to be fastened to the belt members, in such a way that the article will assume a pant shape, where the belt members form a part of the waist portions of the pant; the method comprising:
- double folding the belt members before applying said belt members to the article;
- cutting the double folded belt members in an arcuate shape in which a tangent to the arcuate curve formed by respective longitudinal side edges of the belt portions in the area of the fold makes a substantial right angle to the fold; and
- applying the belt members in their double folded position to the rear portion of the article.

6. The method according to claim 5, wherein the belt members are attached to the rear portion of the article in their double folded position with an easily breakable seal.

* * * * *